(12) United States Patent
Hashimoto et al.

(10) Patent No.: US 10,338,028 B2
(45) Date of Patent: Jul. 2, 2019

(54) ION MOBILITY SEPARATION DEVICE

(71) Applicant: Hitachi, Ltd., Chiyoda-ku, Tokyo (JP)

(72) Inventors: Yuichiro Hashimoto, Tokyo (JP); Hideki Hasegawa, Tokyo (JP); Masao Suga, Tokyo (JP); Hiroyuki Satake, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 331 days.

(21) Appl. No.: 14/905,484

(22) PCT Filed: Jul. 19, 2013

(86) PCT No.: PCT/JP2013/069580
§ 371 (c)(1),
(2) Date: Jan. 15, 2016

(87) PCT Pub. No.: WO2015/008371
PCT Pub. Date: Jan. 22, 2015

(65) Prior Publication Data
US 2016/0153937 A1    Jun. 2, 2016

(51) Int. Cl.
| G01N 27/62 | (2006.01) |
| G01N 33/00 | (2006.01) |
| H01J 49/00 | (2006.01) |

(52) U.S. Cl.
CPC ....... G01N 27/624 (2013.01); G01N 33/0006 (2013.01); H01J 49/0009 (2013.01)

(58) Field of Classification Search
CPC ............... G01N 27/624; G01N 27/622; G01N 33/0006; H01J 49/0009
See application file for complete search history.

(56) References Cited

U.S. PATENT DOCUMENTS

| 4,238,678 A | 12/1980 | Castleman et al. |
| 6,495,823 B1 | 12/2002 | Miller et al. |
(Continued)

FOREIGN PATENT DOCUMENTS

| JP | 2008-508693 A | 3/2008 |
| JP | 2008-527396 A | 7/2008 |
| JP | 2009-522750 A | 6/2009 |

OTHER PUBLICATIONS

Zeev B Alfassi, (On the normalization of a mass spectrum for comparison of two spectra, Journal of the American Society for Mass Spectrometry, vol. 15, Issue 3, 2004, pp. 385-387, ISSN 1044-0305, http://dx.doi.org/10.1016/j.jasms.2003.11.008.(http://www.sciencedirect.com/science/article/pii/S1044030503008444)).*

(Continued)

*Primary Examiner* — Brooke Purinton
(74) *Attorney, Agent, or Firm* — Crowell & Moring LLP (57) ABSTRACT

An ion mobility separation device includes: an ion source that generates an ion; a pair of flat-plate electrodes having an introduction opening and a discharge opening for the ion generated by the ion source; a pump for causing the ion introduced via the introduction opening of the pair of flat-plate electrodes to travel toward the discharge opening; a voltage control unit that applies an asymmetric time-varying voltage and a direct-current voltage to the pair of flat-plate electrodes; a plurality of detectors disposed in a direction orthogonal to both an ion travel direction due to the pump and an applied direction of the asymmetric time-varying voltage; and a signal processing unit that processes a signal detected by the plurality of detectors. The voltage control unit performs a total transmission measurement involving application of the voltages to the pair of flat-plate electrodes so as to generate equal fields at least at two different points in the direction orthogonal to both the ion (Continued)

travel direction due to the pump and the applied direction of the asymmetric time-varying voltage. Compared to conventional technology, both high accuracy and high throughput are achieved in an asymmetric field application-type ion mobility separation device.

11 Claims, 7 Drawing Sheets (56) References Cited

U.S. PATENT DOCUMENTS

| | | | | |
|---|---|---|---|---|
| 2001/0032929 A1* | 10/2001 | Fuhrer | ............... | H01J 49/06 250/281 |
| 2002/0134932 A1* | 9/2002 | Guevremont | ......... | B01D 59/46 250/281 |
| 2007/0176092 A1* | 8/2007 | Miller | ............... | G01N 27/624 250/288 |
| 2008/0149824 A1* | 6/2008 | Miller | ............... | G01N 27/624 250/287 |
| 2008/0191132 A1 | 8/2008 | Boyle et al. | | |
| 2009/0048797 A1* | 2/2009 | Tolmachev | ......... | H01J 49/0009 702/85 |
| 2009/0159796 A1* | 6/2009 | Belford | ............... | G01N 27/624 250/294 |
| 2009/0189064 A1 | 7/2009 | Miller et al. | | |
| 2009/0294644 A1* | 12/2009 | Belov | ............... | G01N 27/622 250/282 |
| 2010/0001182 A1 | 1/2010 | Burchfield et al. | | |
| 2010/0207022 A1 | 8/2010 | Tang et al. | | |
| 2010/0230588 A1 | 9/2010 | Atkinson et al. | | |
| 2012/0298860 A1* | 11/2012 | Park | ............... | H01J 49/0404 250/288 |

OTHER PUBLICATIONS

Buryakov et al., "A New Method of Separation of Multi-Atomic Ions by Mobility at Atmospheric Pressure Using a High-Frequency Amplitude-Asymmetric Strong Electric Field", International Journal of Mass Spectrometry and Ion Processes 128, 1993, pp. 143-148.

International Search Report (PCT/ISA/210) issued in PCT Application No. PCT/JP2013/069580 dated Aug. 20, 2013, with English translation (six (6) pages).

Japanese-language Written Opinion (PCT/ISA/237) issued in PCT Application No. PCT/JP2013/069580 dated Aug. 20, 2013 (seven (7) pages).

* cited by examiner

ION MOBILITY SEPARATION DEVICE

TECHNICAL FIELD

The present invention relates to an ion mobility separation device.

BACKGROUND ART

Ion mobility separation devices that separate and detect ions by ion mobility have characteristics enabling operation without requiring a vacuum pump and even under an atmospheric pressure, and are for this reason widely utilized as on-site measurement devices for environment analysis, explosives detection, illegal drugs detection, chemical agents detection and the like. In the ion mobility separation devices, the technology for highly accurately separating ions generated by an ion source and then detecting the ions with high sensitivity and high throughput is an important issue to be addressed for further expanding applications and reducing false detection.

In Patent Literature 1, there is described a time-of-flight ion mobility separation device and a method whereby ions generated by an ion source are accelerated at a certain timing and are then separated based on the difference in the time of arrival at a detector. The ions can be separated by utilizing the characteristics of various ion species having different ion mobilities, whereby a chemical substance can be identified and quantitated.

In Non Patent Literature 1, there is described an asymmetric field application-type ion mobility separation device. In this method, ions are separated by utilizing a change in ion mobility that is caused upon application of a high electric field of 20 kV/cm or above to the ions. The ion mobility change caused by the high field application differs depending on the ion species. Accordingly, when an asymmetric high frequency field is applied between separation electrodes, a deflection unique to the particular ion species is caused. Thus, it is necessary to apply a compensation field for compensating for the deflection between the electrodes so as to allow the ions to travel straight between the separation electrodes without colliding therewith. By setting the compensation field to a specific value, only a specific ion can be allowed to pass and be detected. In addition, by scanning the compensation field, it becomes possible to acquire a complete spectrum.

In Patent Literature 2, there is described a method for achieving reduced size and increased throughput of the ion mobility separation device described in Non Patent Literature 1 by using a flat-plate insulator member of glass and the like. By using the flat-plate insulator member, manufacturing can be made easier. In this patent literature, it is also described that a gas flow path, separation electrodes, and current detection electrodes are arranged in parallel and given respectively separate parameters so as to simultaneously monitor ions under a plurality of different transmission conditions and achieve high throughput. In addition, a method for enhancing ion separation capability by installing a plurality of current detection electrodes in an ion travel direction is also described.

In Patent Literature 3, a method is described whereby, after asymmetric field application-type ion mobility separation, time-of-flight ion mobility separation is performed. Because asymmetric field application-type ion mobility separation and time-of-flight ion mobility separation have different ion separation characteristics, an improvement in ion separation capability can be obtained compared with when an asymmetric field application-type ion mobility separation device or a time-of-flight ion mobility separation device is used individually.

CITATION LIST

Patent Literature

Patent Literature 1: U.S. Pat. No. 4,238,678
Patent Literature 2: U.S. Pat. No. 6,495,823
Patent Literature 3: U.S. Patent Publication No. 2010-0001182

Non Patent Literature

Non Patent Literature 1: Int. J Mass Spectrometry, 1993, v128, 143-148

SUMMARY OF INVENTION

Technical Problem

In an ion mobility detector that separates and detects ions by ion mobility, a technology for separating and detecting the ions generated by an ion source with high sensitivity, high accuracy, and high throughput is important. Particularly, in an asymmetric field application-type ion mobility detector, increasing ion separation capability and increasing throughput have been mutually conflicting factors. Namely, setting a compensation field finely so as to increase ion separation capability is associated with an increase in the scan time for a measurement condition, resulting in a decrease in throughput.

In Patent Literature 1, an asymmetric field application-type ion mobility detector is not described.

In Non Patent Literature 1, if the compensation voltage is finely set in order to increase ion separation capability, the scan time for compensation voltage becomes increased, resulting in a decrease in throughput.

In Patent Literature 2, while it is described that an increase in throughput is achieved by a parallel arrangement of the separation electrodes, flow path, and detector, such parallel arrangement leads to an increase in the size of the ion source or the separation electrodes. As a result, a significant non-uniformity is caused in the amount of ion supplied from the ion source to the separation electrodes. Accordingly, sensitivity greatly varies depending on the position of the detector, resulting in a decrease in measurement accuracy.

In Patent Literature 3, there is a problem similar to that of Patent Literature 1; namely, if the compensation voltage is finely set with respect to the asymmetric field application-type ion mobility detector, an increase in the scan time for compensation voltage is caused, resulting in a decrease in throughput.

Solution to Problem

The problems are solved as follows. In order to improve measurement value accuracy even when a plurality of detection electrodes are provided, with respect to a signal strength at the time of normal signal reading, a potential difference applied between separation electrodes is made constant regardless of the position in a direction orthogonal to both an ion travel direction and an asymmetric field applied direction, a signal strength of signal reading under a total transmission condition is acquired, and this signal strength is used for correcting the signal strength obtained by the normal measurement.

Specifically, there is provided an ion mobility separation device including an ion source that generates an ion; a pair of flat-plate electrodes having an introduction opening and a discharge opening for the ion generated by the ion source; a pump that causes the ion introduced from the introduction opening of the pair of flat-plate electrodes to travel toward the discharge opening; a voltage control unit that applies an asymmetric time-varying voltage and a direct-current voltage to the pair of flat-plate electrodes; a plurality of detectors disposed in a direction orthogonal to both an ion travel direction due to the pump and an applied direction of the asymmetric time-varying voltage; and a signal processing unit that processes a signal detected by the plurality of detectors. The voltage control unit performs a total transmission measurement involving application of the voltages to the pair of flat-plate electrodes so as to generate equal fields at least at two different points in a direction orthogonal to both the ion travel direction due to the pump and the applied direction of the asymmetric time-varying voltage.

Advantageous Effects of Invention

According to the present invention, both high accuracy and high throughput are achieved in an asymmetric field application-type ion mobility separation device.

DESCRIPTION OF EMBODIMENTS

First Embodiment

Figure 1:
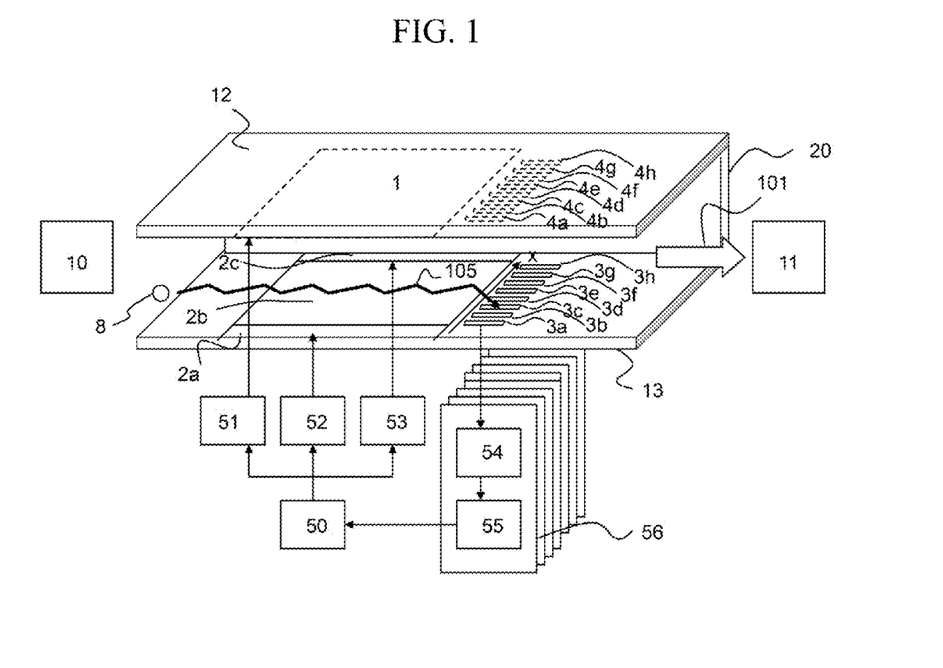
FIG. 1 illustrates a first embodiment of the present system.

FIG. 1 is a configuration diagram of an ion mobility separation device to which the present system is applied. Ions 8 generated by an atmospheric pressure ion source 10, such as an atmospheric pressure chemical ion source; an atmospheric pressure photo-excited ion source; an electrospray ion source; or a dielectric-barrier discharge ion source, are introduced into a space enclosed by a substrate 12, a substrate 13, and spacers 20 (a spacer on the front side not shown), by a gas flow 101 caused by a pump 11 comprising a diaphragm pump and the like.

The substrate 12 and the substrate 13 may be made of an insulator, such as glass, plastic, ceramic and the like given the need for placing various electrodes on their surfaces, whereby manufacturing can be facilitated. On the substrates 12 and 13, separation electrodes 1 and 2 are respectively affixed or coated in the form of thin-film electrodes. The substrate 12 and the substrate 13 are disposed at an interval d, which is normally on the order of 50 um to 2 mm. The greater the interval d, the higher the voltage values will disadvantageously become that are required as a separation voltage and a compensation voltage, as will be described later. The smaller the interval d, the smaller the ion transmission rate will disadvantageously become due to, e.g., turbulence near a wall surface, ion diffusion, or motion of ions by the separation voltage between the separation electrodes.

The ions 8 travel in a travel direction 105 by a combined force of force received from the gas flow 101 and an asymmetric electric field and a compensation electric field formed by power supplies 51, 52, and 53 between the separation electrodes 1 and 2. Namely, the ions 8 are subjected to a force due to the electric fields causing the ions to move in directions perpendicular to the substrates 12 and 13, and to a force by the gas flow 101 causing the ions to move in the pump 11 direction. The passing time t of the ions between the separation electrodes 1 and 2 is on the order of several ms to several 100 ms, which is determined by $t=F/dwl$ where F is the gas flow rate by the pump; d is the interval between the separation electrodes; w is the depth between the separation electrodes; and l is the length in the travel direction between the separation electrodes. The shorter the passing time, the higher the transmission rate will advantageously become; the longer the passing time, the higher the resolution that is obtained will advantageously become.

The ions that have passed between the separation electrodes 1 and 2 reach a positive ion detection electrode 3 if they are positive ions, or a negative ion detection electrode 4 if they are negative ions. In order to allow the ions to reach the detection electrodes efficiently, a direct-current voltage on the order of several to several tens of volts is applied between the positive ion detection electrode 3 and the negative ion detection electrode 4. The ions that have reached the detection electrodes are sent to a signal processing unit 56, amplified by a weak current amplifier 54, and then recorded in a recorder 55 as a signal. While not shown in FIG. 1, the ions that have not passed between the electrodes lose their charges upon arrival at the substrate 12 or substrate 13, and are therefore not detected as signals. While FIG. 1 only shows the signal processing unit for the positive ions, the negative ions are subjected to a similar signal processing sequence after their arrival at the negative ion detection electrode 4.

Figure 2:
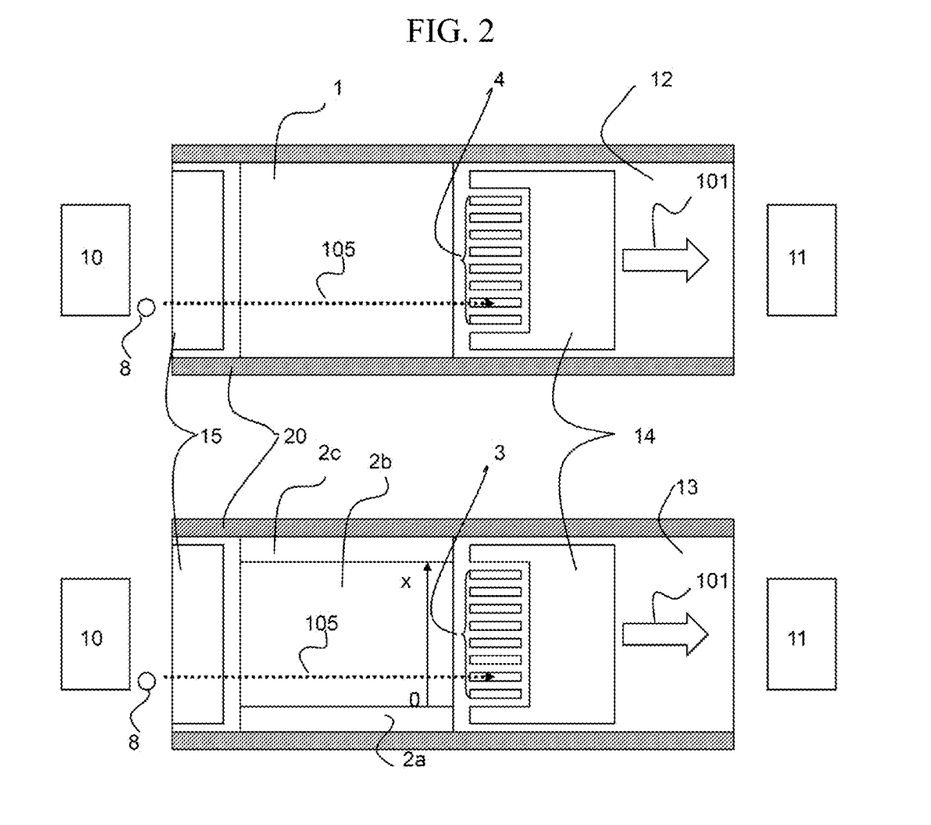
FIG. 2 illustrates the first embodiment of the present system

With reference to FIG. 2, a supplementary description of the first embodiment will be given. FIG. 2 shows plan views of the substrate 12 and substrate 13 taken across FIG. 1 in a plane parallel with the substrate 12. The ions 8 travel along the gas flow 101 in the ion travel direction 105. Because the flow of gas is disturbed near the spacers 20, it is desirable to use the ion separation portion at a location not in the vicinity of the spacers 20 (around 2d). In this case, the detection electrodes 3 and 4 may be installed at locations other than the vicinity of the spacers so as to decrease the number of the detection electrodes and the signal processing units. Alternatively, the separation electrodes may be divided into high conductivity portions (2a, 2c) and a low conductivity portion (2b), whereby the voltage values applied to these portions can be reduced. The high conductivity portions (2a, 2c) may be made of metal, while the low conductivity portion (2b) may be made of a metal oxide thin-film or organic conductive material. The low conductivity portion (2b) has an end-to-end resistance on the order of 50Ω to 10 kΩ. As the end-to-end resistance is increased, the influence of the surrounding electric noise also increases, or the separation voltage becomes distorted at around the center disadvantageously. As the end-to-end resistance is reduced, electric power consumption increases, which is associated with a risk of damage to the separation electrode 2 due to increased temperature.

If charge-up is caused by the ions colliding with the insulator, the ion transmission rate may become decreased or ion separation performance may become lowered. Accordingly, by installing the electrode 14 and the electrode 15 at portions proximate to the ion passage route on the substrate 12 and the substrate 13, charge-up can be prevented.

Figure 3:
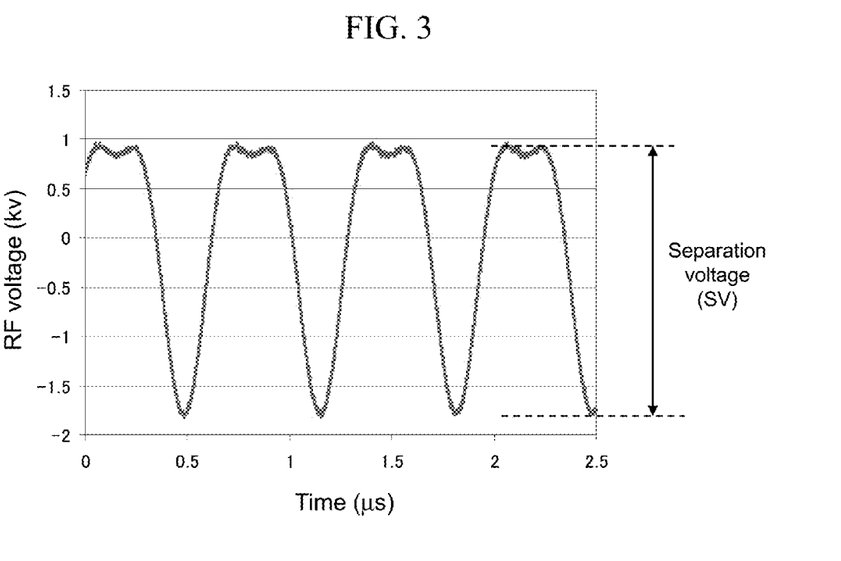
FIG. 3 is a diagram for describing the first embodiment of the present system.

Between the separation electrode 1 and the separation electrode 2, a combined. voltage of a separation voltage (SV), which is an asymmetric voltage, and a compensation voltage (CV) is applied by the power supplies 51, 52, and 53. FIG. 3 illustrates an example of the applied separation voltage.

The separation voltage (SV) is expressed by Expression 1, and is a sum of sine waves of frequencies 1.5 MHz and 3 MHz.

$$SV=V\text{main}\sin(2\pi ft)+V\text{sub}\sin(2\pi(2f)t+\varphi) \quad \text{(Expression 1)}$$

The separation voltage (SV) that is an asymmetric voltage may have other variations, such as square waves. However, by using a high frequency and its harmonics as described above, an asymmetric voltage on the order of several kV can be relatively easily generated by a single coil.

The compensation voltage (CV), which varies depending on the position in the x-direction (see FIG. 2), is expressed by Expression 2:

$$CV(x)=Va+(Vc-Va)x/s \quad \text{(Expression 2)}$$

where Va and Vc are respectively voltages applied to 2a and 2c, and s is the width of the low conductivity portion 2b. The voltage applied to 2a and 2c is voltage ΔCV(=Vc−Va). Thus, because the compensation voltage varies depending on the position in the direction (x-direction: see FIG. 2) orthogonal to both the ion travel direction due to gas flow and the asymmetric field applied direction, spectrum information at different compensation voltages can be simultaneously obtained by placing a plurality of detectors in the x-direction.

Of the amount of ion that is actually produced by the ion source 10, the amount of ion that reaches the detectors varies depending on the position in the direction (the x-direction) orthogonal to both the ion travel direction due to gas flow and the asymmetric field applied direction, which is a problem. Accordingly, it is necessary to correct this non-uniformity by a. system described below.

Figure 4:
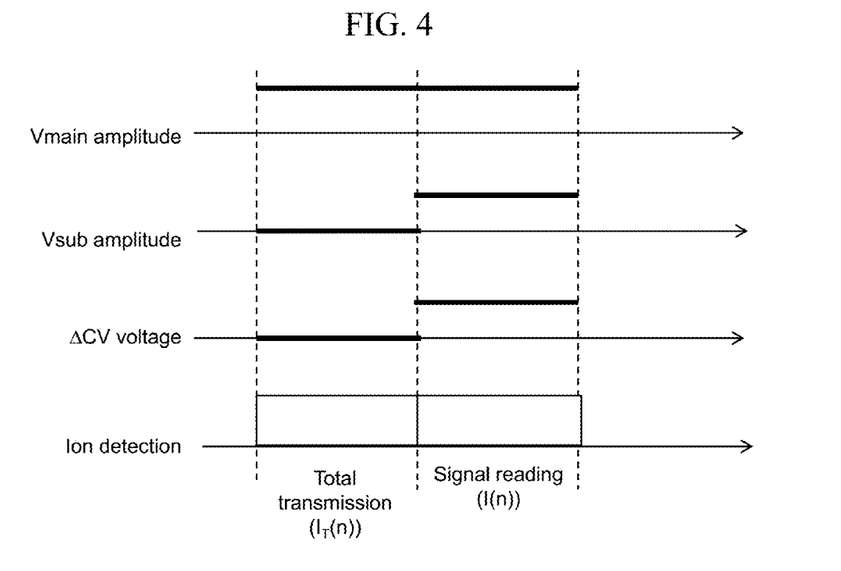
FIG. 4 is a diagram for describing the first embodiment of the present system.

FIG. 4 shows a typical measurement sequence of the present correction system. In addition to normal signal reading, the amount of ion under a total transmission condition is measured before or after (not shown) the normal signal reading. In FIG. 4, the total transmission condition refers to a measurement condition under a certain field condition at least at two different points in the x-direction. When the amount of signal under the total transmission condition is $I_T(n)$, and the signal strength at the time of normal signal reading is I(n), the transmission rate F after correction is calculated according to $$F=I(n)/I_T(n) \quad \text{(Expression 3)}$$

and used for quantitative or qualitative determination. In order to measure the amount of signal under the total transmission condition, it is necessary to set the ΔCV voltage to effectively 0 V for measurement. By setting either the Vsub voltage amplitude or Vmain voltage to 0 V, all of the ions can be caused to travel along a trajectory around the center of the flat-plate electrodes without deflection regardless of the ion species. While FIG. 4 illustrates the case in which only Vsub voltage is set to 0 V for measurement, either Vsub or Vmain may have an applied voltage or neither may have an applied voltage. Under such conditions, the ions will have the same transmission condition regardless of their position in the x-direction, whereby an amount of signal proportional to the amount of ion supplied from the ion source can be obtained.

The signal reading under the total transmission condition with respect to the normal signal reading may be performed each time, or, if the ion source variation is small, a signal reading result under the total transmission condition may be used for correcting a plurality of signal reading results. In this case, the total measurement time can be decreased compared with when the signal reading under the total transmission condition is performed each time.

Figure 5A:
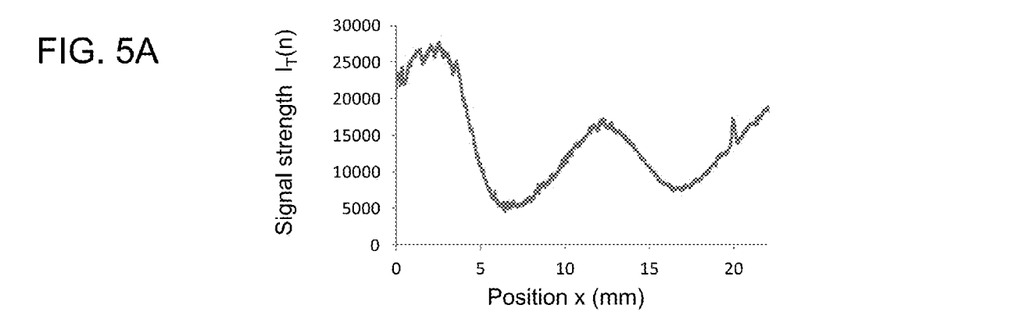
FIGS. 5A-5C are diagrams for describing the effect of the first embodiment of the present system.
Figure 5B:
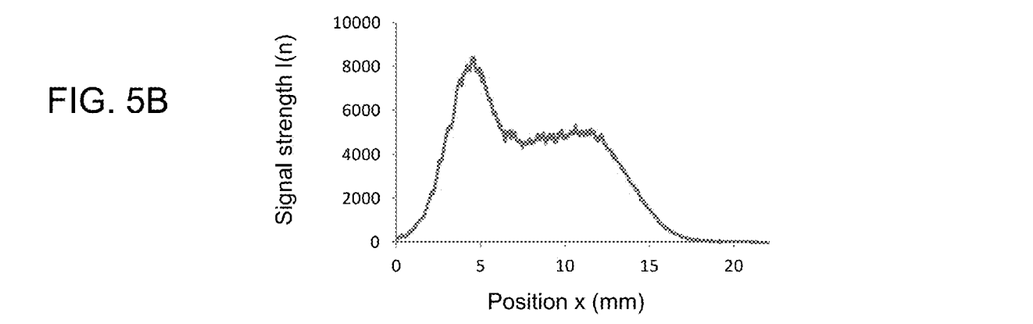
Figure 5C:
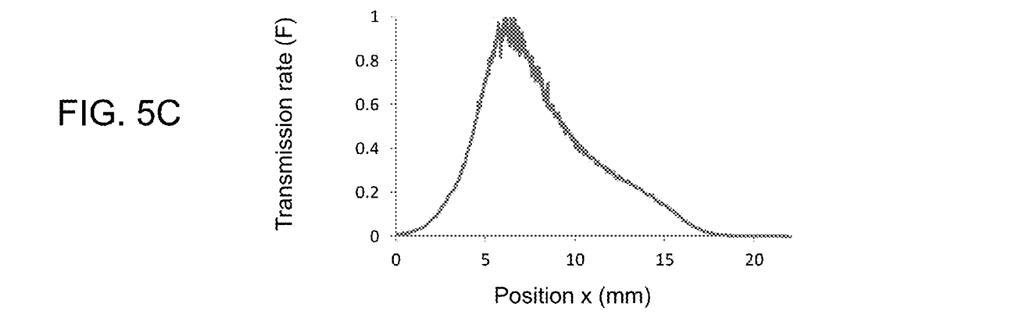

FIG. 5 shows diagrams illustrating the effect of application of the present measurement system (the sample is a reserpine molecular ion). FIG. 5(A) shows the signal strength $I_T(n)$ under total transmission condition; FIG. 5(B) shows the signal strength I(n) at the time of normal signal reading; and FIG. 5(C) shows the transmission rate F after correction. In FIG. 5(B), the signal strength I(n) at the time of normal signal reading has two peaks at around 4.8 mm and 11.2 mm; after correction, a single peak is observed at around 5.5 mm. The result after correction agrees well with a conventional FAIMS result, indicating that an accurate measurement can be performed with the present measurement system.

Figure 6:
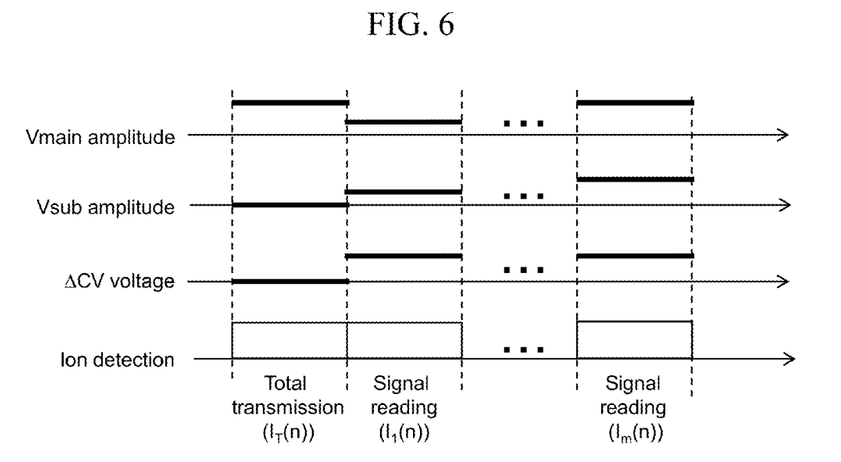
FIG. 6 is a diagram for describing the first embodiment of the present system.

It is also possible, as shown in FIG. 6, to calculate the transmission rate Fm with respect to a plurality of signal strengths $I_m(n)$ under different measurement conditions according to $$Fm=Im(n)/I_T(n) \quad \text{(Expression 4)}.$$

When normal signal reading is performed under a plurality of voltage conditions, signal reading under the total transmission condition may be performed with respect to each. Alternatively, it is also possible, as shown in FIG. 6, to use a single result of signal reading under the total transmission condition for correcting a plurality of signal reading results. In this case, the signal reading under the total transmission condition may be performed with respect to each voltage condition, whereby the total measurement time can be decreased.

Figure 7:
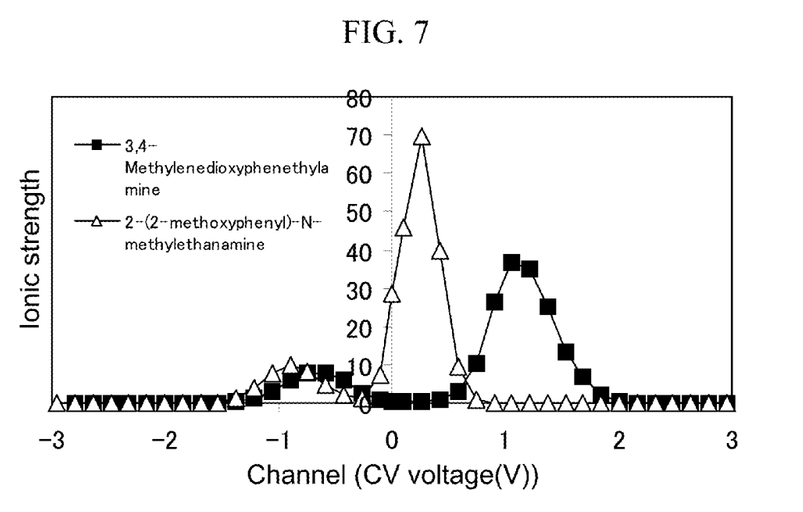
FIG. 7 is a diagram for describing the effect of the first embodiment of the present system.

FIG. 7 is a diagram illustrating the utility of the present system, showing an example of detection with the positive ion detection electrode 3 (approximately 39 channels) upon application of SV=2.1 kV, Va=−3 V, and Vc−3 V. As the samples, 2-(2-methoxyphenyl)-N-methylethanamine molecular ion and 3,4-Methylenedioxyphenethylamine molecular ion, which have close mass numbers and similar molecular structures, were measured. At around CV=0.2 V, only the 2-(2-methoxyphenyl)-N-methylethanamine molecular ion is strongly detected, whereas at around CV=1.1 V, only the 3,4-Methylenedioxyphenethylamine molecular ion is strongly detected. Thus, it can be seen that sufficient separation capability for separating the two types of ions is available. In a conventional example, it has taken a long time to acquire similar data because the compensation voltage is temporally scanned from −3 V to 3 V. By using the present technology, the transmission characteristics data at different compensation voltages can be simultaneously detected, whereby an increase in speed by a factor of 10 or more can be achieved.

Second Embodiment

Figure 8:
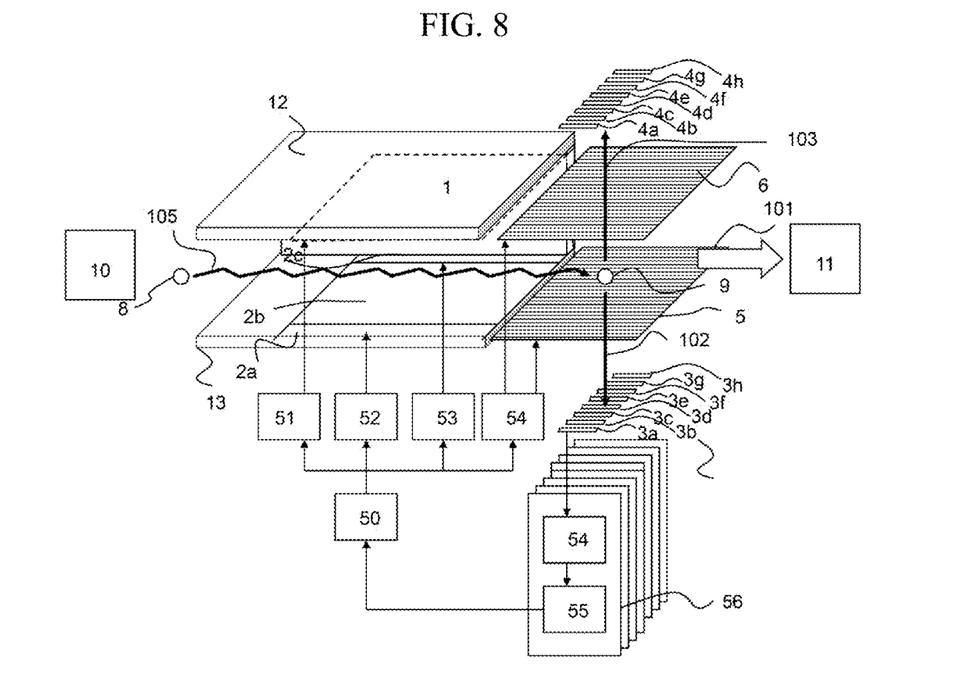
FIG. 8 illustrates a second embodiment of the present system.

FIG. 8 is a configuration diagram of an ion mobility separation device according to a second embodiment in which the present system is applied. The present embodiment is similar to the first embodiment up until the ions from the ion source pass between the separation electrodes 1 and 2. In the present embodiment, after the passage between the separation electrodes 1 and 2, time-of-flight ion mobility separation is performed in combination. Between mesh electrodes 5 and 6, a direct-current pulse voltage is applied at the intervals of several Hz to several 100 Hz. As a result, ions 9 that have passed through the separation electrodes 1 and 2 are accelerated in a travel direction 102 if the ion is a positive ion or in a travel direction 103 if the ion is a negative ion. Between the mesh electrode 5 and the detection electrode 3, and between the mesh electrode 6 and the detection electrode 1, there are respectively formed electric fields parallel with the respective travel directions. The parallel electric fields may be generated using a flat-plate electrode or a member coated with conductive material, which are not shown. In the parallel electric fields, the greater the ion mobility of the ion, the faster the ion travels. Accordingly, by measuring the time of flight, separation of ion species by ion mobility can be performed. In addition, according to the present embodiment, conditions with different compensation voltages can be set depending on the position in the x-direction, so that the compensation voltage condition and the time of flight can be simultaneously acquired with respect to the ions.

Figure 9:
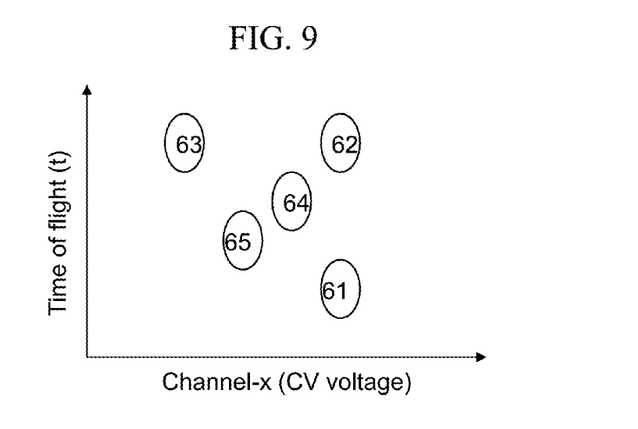
FIG. 9 is a diagram for describing the effect of the second embodiment of the present system.

FIG. 9 is a diagram for describing the effect of the present system, showing an example in which as samples, five types of ions A to E were detected. Signals arising from the ion species A to E are respectively indicated by 61 to 65 in the diagram. While the signal 61 arising from ion species A and the signal 62 arising from ion species B cannot be separated in the x-coordinate of the detection electrode (corresponding to the compensation voltage), they can be separated by the time of flight. Meanwhile, while the signal 63 arising from ion species C and the signal 62 arising from ion species B cannot be separated by the time of flight information, they can be separated by the x-coordinate of the detection electrode (corresponding to the compensation voltage). Thus, according to the present embodiment, measurement can be performed with high two-dimensional separation performance in a short time.

In the second embodiment, too, there is the same issue that the amount of ion produced from the ion source 10 that reaches the detector varies depending on the position in the x-direction (see FIG. 2). Accordingly, it is also effective in the present embodiment to correct the non-uniformity by the system of the first embodiment. Namely, by correcting the signal strength at the time of normal signal reading with the signal strength of the signal reading under the total transmission condition where the potential difference applied between the divided separation electrodes 1 and 2 is constant regardless of the position in the x-direction, an accurate measurement value can be obtained.

Third Embodiment

Figure 10:
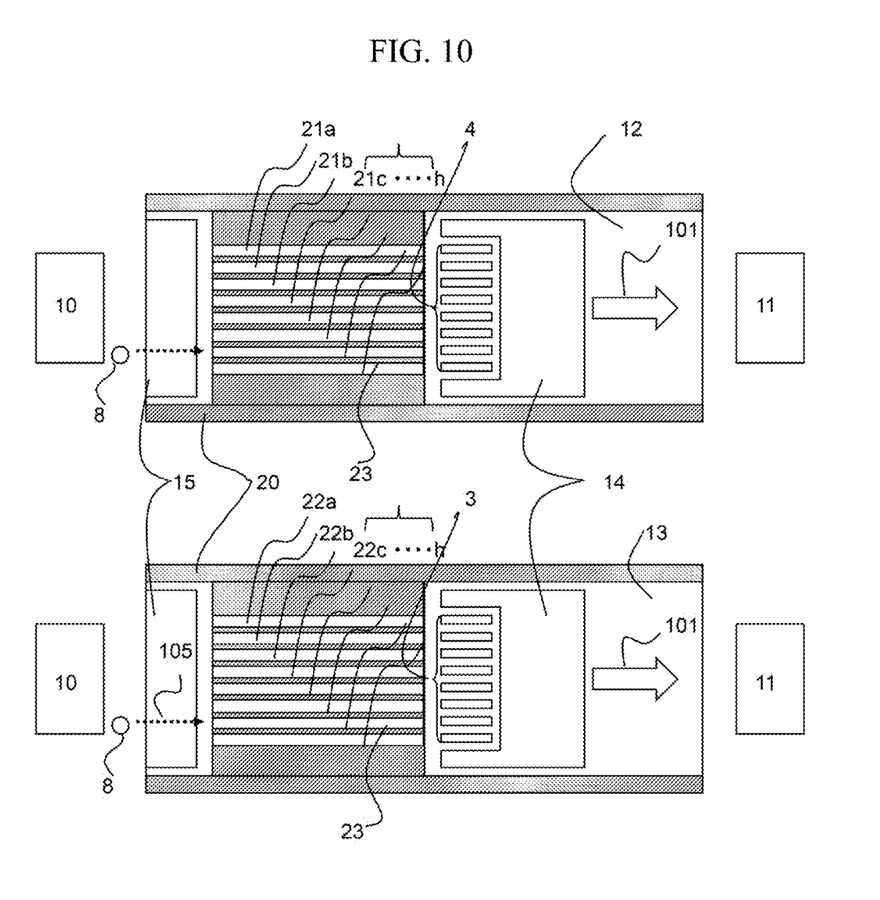
FIG. 10 is a third embodiment of the present system.

FIG. 10 is a configuration diagram of an ion mobility separation device according to a third embodiment in which the present system is applied. The present embodiment illustrates a case in which the ion separation portions are isolated by spacers 23. The present embodiment differs from the first embodiment in that independent voltages can be applied to the separation electrodes 21 and 22. Accordingly, when only the known SV and CV are measured, measurement can he performed in a shorter time than according to the first embodiment. In the third embodiment, too, there is the issue that the amount of ion generated from the ion source 10 that reaches the detector varies depending on the position in the x-direction. Accordingly, it is also effective in the present embodiment to correct the nonuniformity by the system of the first embodiment. Namely, by correcting the signal strength at the time of normal signal reading with the signal strength of the signal reading under the total transmission condition where the potential difference applied between the divided separation electrodes 21 and 22 is constant regardless of the position in the x-direction, an accurate measurement value can be obtained. In this case, by equally setting the potentials between 21*a*-22*a*, 21*b*-22*b*, . . . , and 21*h*-22*h*, the signal reading under the total transmission condition can be performed.

While the example has been described in which the ion mobility separation mechanism is installed at atmospheric pressure, it is also possible to install the present separation device at low vacuum or under high pressure such that ion mobility separation is enabled.

While the present embodiment has been described with reference to a combination of a sensing ammeter as a detector and a weak current amplifier, it is also possible to use a combination with other ion detect systems including a semiconductor detector or an electron multiplier.

Fourth Embodiment

In order to increase a measurable dynamic range, it is also effective to determine the integrated time at the time of normal signal reading using the signal strength under the total measurement condition. For example, when a CCD detector is used as the detector, there is a limit to the amount of charge that can be normally accumulated in an electrode. Accordingly, the integrated time at the time of normal signal reading is determined such that the range is not exceeded. Specifically, the signal strength $I_T(n)$ under the total measurement condition is integrated for a sufficiently short time (such as 1 ms). Because the signal strength $I(n)$ at the time of normal signal reading becomes smaller than the signal strength $I_T(n)$ under the total measurement condition, the signal strength at the time of normal signal reading is determined such that $I_T(n)$ does not exceed the permitted amount of charge of the CCD detector. In this way, the integrated time can be set longer when the amount of ion is large, or shorter when the amount of ion is small, whereby an increase in measurable dynamic range can be achieved. Such measurement is also effective in the case of other types of current detectors, such as a CMOS type, in addition to the CCD detector.

REFERENCE SIGNS LIST

1 Separation electrode
2 Separation electrode
3 Detection electrode (for positive ion)
4 Detection electrode (for negative ion)
5 Mesh electrode
6 Mesh electrode
8 Ion
9 Ion
10 Ion source
11 Pump
12 Substrate
13 Substrate
14 Electrode 15 Electrode
20 Spacer
21 Divided separation electrode
22 Divided separation electrode
23 Spacer
50 Control unit
51 Power supply
52 Power supply
53 Power supply
54 Amplifier
55 Data recorder
56 Signal processing unit
61 Signal derived from sample A
62 Signal derived from sample B
63 Signal derived from sample C
64 Signal derived from sample D
65 Signal derived from sample E
101 Gas flow direction
102 Ion travel direction
103 Ion travel direction
105 Ion travel direction

The invention claimed is:

1. An ion mobility separation device comprising:
an ion source that generates ions;
a pair of flat-plate electrodes having an introduction opening and a discharge opening for the ions generated by the ion source;
a pump that causes the ions introduced from the introduction opening of the pair of flat-plate electrodes to travel toward the discharge opening;
a controller programmed to apply an asymmetric time-varying voltage and a direct-current voltage to the pair of flat-plate electrodes;
a plurality of detectors disposed in a direction orthogonal to both an ion travel direction due to the pump and an applied direction of the asymmetric time-varying voltage; and
a processor programmed to process a signal detected by the plurality of detectors,
wherein, to obtain a total transmission measurement of the ions at the plurality of detectors, the controller controls application of a potential difference between the flat-plate electrodes such that all of the ions are caused to travel along a trajectory between the flat-plate electrodes without deflection, which is a total transmission condition of the ions, by generating equal fields at least at two different points in the direction orthogonal to both the ion travel direction due to the pump and the applied direction of the asymmetric time-varying voltage.

2. The ion mobility separation device according to claim 1, wherein the processor corrects a signal strength obtained upon application of the asymmetric time-varying voltage and the direct-current voltage during a normal condition, based on a signal strength obtained during the total transmission measurement.

3. The ion mobility separation device according to claim 2, wherein the processor calculates, during the signal strength correction, the ratio of a signal strength obtained upon application of the asymmetric time-varying voltage and the direct-current voltage and the signal strength obtained by the total transmission measurement.

4. The ion mobility separation device according to claim 2, wherein, during the total transmission measurement, a field formed by the asymmetric time-varying voltage and/or the direct-current voltage is made effectively zero.

5. The ion mobility separation device according to claim 1, wherein the controller applies a direct-current compensation field that varies depending on the position in the direction orthogonal to both the ion travel direction and the applied direction of the asymmetric time-varying voltage.

6. The ion mobility separation device according to claim 5, wherein a conductive resistive film with a resistance value of 50Ω to 10 kΩ is used for forming a direct-current electric field, depending on the position orthogonal to both the ion travel direction and the asymmetric voltage.

7. The ion mobility separation device according to claim 1, wherein the controller is programmed to accelerate the ion that has passed the pair of flat-plate electrodes in a direction orthogonal to the flat-plate electrodes, and the signal processor measures the time of flight before the ion reaches the plurality of detectors.

8. The ion mobility separation device according to claim 1, wherein the flat-plate electrodes are divided into a plurality of sections, and the controller has a timing for applying a different asymmetric time-varying voltage and direct-current voltage for each of the sections.

9. The ion mobility separation device according to claim 1, wherein the detector is a CCD detector, and the processor determines, based on a signal during the total transmission measurement, the integrated time of a signal obtained upon application of the asymmetric time-varying voltage and the direct-current voltage.

10. The ion mobility separation device according to claim 1, wherein the plurality of detectors includes a plurality of first detectors disposed adjacent to one of the pair of flat-plate electrodes and a plurality of second detectors disposed adjacent to another of the pair of flat-plate electrodes.

11. The ion mobility separation device according to claim 10, wherein the first detectors are disposed in a first row and the second detectors are disposed in a second row.

* * * * *